US006281349B1

(12) United States Patent
Pulleyblank (10) Patent No.: US 6,281,349 B1
(45) Date of Patent: Aug. 28, 2001

(54) METHOD FOR NUCLEIC ACID PURIFICATION USING IODINE

(76) Inventor: David E. Pulleyblank, 408 Euclid Avenue, Toronto, Ontario (CA), M6G 2S9

( * ) Notice: Subject to any disclaimer, the term of this patent is extended or adjusted under 35 U.S.C. 154(b) by 0 days.

(21) Appl. No.: 09/640,377

(22) Filed: Aug. 17, 2000

Related U.S. Application Data (60) Provisional application No. 60/149,292, filed on Aug. 18, 1999.

(51) Int. Cl.[7] .............................. C07H 21/04; C12N 15/00
(52) U.S. Cl. ....................................... 536/25.4; 435/320.1
(58) Field of Search ........................ 435/320.1; 536/25.4

(56) References Cited

U.S. PATENT DOCUMENTS

| | | | |
|---|---|---|---|
| 4,946,673 | * 8/1990 | Pollack et al. | 424/80 |
| 5,561,064 | 10/1996 | Marquet et al. | 435/320.1 |
| 5,660,984 | 8/1997 | Davis et al. | 435/6 |
| 5,707,812 | 1/1998 | Horn et al. | 435/6 |
| 5,989,431 | * 11/1999 | Evans et al. | 210/645 |

OTHER PUBLICATIONS

Sambrook et al. 1989. Molecular Cloning, A Laboratory Manual, Second edition. pp. 1.40–1.41.*
Wilson. 1993. BioTechniques 15:414–422.*
Ishizawa et al. 1991. Nucleic Acids Research 19: 5792.*
Vogelstein et al. 1979. Proc. Natl. Acad. Sci. USA. 76:615–619.*

* cited by examiner

*Primary Examiner*—James Ketter
*Assistant Examiner*—Lisa Gansheroff
(74) *Attorney, Agent, or Firm*—Sim & McBurney (57) ABSTRACT

The present invention provides a novel method for the purification of plasmid nucleic acid preparations. More specifically, the present invention provides a novel method using iodine for purifying plasmid nucleic acid suitable for several different applications in molecular biology.

20 Claims, 8 Drawing Sheets

METHOD FOR NUCLEIC ACID PURIFICATION USING IODINE

RELATED APPLICATIONS

This application claims priority from U.S. Ser. No. 60/149,292 filed Aug. 18, 1999, now abandoned.

FIELD OF THE INVENTION

The present invention relates to a novel method for the purification of nucleic acid preparations. More specifically, the present invention provides a novel method using iodine for purifying plasmid nucleic acid suitable for several different applications in molecular biology.

BACKGROUND OF THE INVENTION

Preparation of plasmid DNA has become a central protocol in modern molecular biology. Conventional existing techniques for the isolation of plasmid DNA from cells include alkaline lysis, lithium miniprep, boiling miniprep and triton-lysozyme lysis. Such techniques have various limitations such as being time-consuming, complex or simply not suitable for large scale manufacturing processes. Also, these techniques tend to yield an impure DNA product. For example, in the alkaline lysis method, the denatured closed circular form of plasmid DNA formed during the procedure often contaminates the resultant plasmid.

Still other types of methods have also been developed for the isolation of plasmid DNA samples. For example, U.S. Pat. No. 5,561,064 describes a method for producing plasmid DNA which incorporates chromatography for purification. U.S. Pat. No. 5,660,984 describes a method and apparatus for isolating a plasmid DNA sample in which an anion-exchange resin is utilized. U.S. Pat. No. 5,707,812 describes a method for purifying plasmid DNA which also incorporates column chromatography for purification.

Commercial kits have also been specifically designed for the isolation of plasmid DNA and now represent a market worth many millions of dollars per year. For academic laboratories stressed by restricted fiscal resources these kits represent a substantial cost which must be considered against the additional time required for the older, more complex protocols. Most of these kits share a number of steps derived from the alkaline lysis protocol of Bimboim and Doly (1) which has subsequently been improved by the addition of a step in which the DNA is separated from other cellular components while adsorbed to a resin, (usually silica particles). This added step improves the purity of the product by removing some residual protein and most of the residual RNA.

Despite the improved quality of plasmid DNA isolated by existing commercial methods, preparations from many *E. coli* strains are contaminated by trace amounts of an extremely stable nuclease, namely Endonuclease I (Endo I) and pancreatic ribonuclease introduced in these methods for the purpose of degrading cellular RNA. Endo I, like many other nucleases, is inactive until magnesium is added to the DNA as required by most DNA metabolizing enzymes. The degradation of the plasmid that this enzymatic contamination causes a serious problem if the DNA is to be used in most molecular biology protocols. When recognized the problem may be overcome through the use of an Endo I negative *E coli* host for the plasmid or through the inclusion of additional steps such as phenol extraction step in the procedure. Such steps such are required whenever it is necessary to transcribe the plasmid since pancreatic ribonuclease, used to reduce contamination of the plasmid by cellular RNA, is sufficiently stable that it can survive the chaotropic solvents used to bind the DNA to the silica matrix.

These modifications to existing conventional protocols are inconvenient. There is no simple selection by which an Endo I deficient mutant of *E. coli* can be derived from a strain with otherwise desired genotypic characteristics. Phenol extraction is especially time consuming since it requires careful separation of the phases and subsequent complete removal of the phenol. Phenol is also hazardous.

There was therefore a need to develop a reliable, fast, efficient and economical method for the preparation of plasmid nucleic acid that obviated at least one of the limitations of the methods of the prior art.

SUMMARY OF THE INVENTION

The present invention provides an improved and rapid method for the preparation of plasmid nucleic acid in which iodine is used to eliminate residual traces of non-specific deoxyribonuclease and ribonuclease that frequently contaminate plasmid nucleic acid preparations made by conventional rapid techniques. The method also optimizes lysis conditions to prevent permanent denaturation of plasmid nucleic acid and improves conditions for selective precipitation of DNA by polyethyleneglycol in the presence of RNA. Plasmids prepared by this method are sufficiently stable that they may be stored in solution at room temperature for months or even years.

The novel method of the invention has advantages for the preparation of plasmid nucleic acid that are irrespective of any need to eliminate nucleases. If the host expresses Endo I or other similar nuclease it is eliminated through chemical modification of amino acid residues contained therein. In the present method iodine and, optionally cesium ions, cause the precipitate of cellular components other than plasmid to be more cohesive and more dense than those formed in other protocols and so this precipitate is more easily removed by centrifugation. Formation of the denatured closed circular form (form IV), which often contaminates plasmid samples prepared by other alkaline techniques is avoided.

Ribonuclease A, used in most protocols to destroy cellular RNA, is not a requirement of the present method, although slightly greater purity may be obtained if its use is included. When ribonuclease is used in the present method it is inactivated and therefore is unlikely to present a problem for subsequent use of the DNA in in vitro transcription experiments.

Sample handling, an important issue when comparing protocols because much time can be lost in changing pipette tips or in moving sample between containers while avoiding disturbance of loose pellets, is minimized. There is only one transfer of sample between centrifuge containers which can be accomplished by pouring. Reagent volumes have been adjusted to simple multiples of a unit volume to permit semi-automated pipetting with an inexpensive repeating pipettor. The procedure requires only a bench top centrifuge or filtration apparatus and no expensive reagents. Furthermore the method can be scaled up to either large volumes of culture or to large numbers of samples without difficulty. The method can be completed in less than 30 minutes with as many samples as can be conveniently centrifuged or filtered while working entirely at room temperature.

The resultant nucleic acid product is essentially free of RNA and is sufficiently pure that it can be used in molecular biological protocols including subcloning and DNA sequence analysis.

In accordance with an object of an aspect of the present invention is a method for preparing plasmid nucleic acid from a host cell, the method comprising: lysing host cells containing said plasmid nucleic acid; providing iodine in sufficient quantity to inactivate nucleases and precipitate host cell nucleic acid and protein, leaving a supernatant containing the plasmid nucleic acid; precipitating the plasmid nucleic acid from the supernatant; and isolating the plasmid nucleic acid.

In one embodiment of the method of the invention the solution of iodine together with a buffer containing a potassium or a cesium salt is added in sufficient quantity to permanently inactivate nucleases and to precipitate the host cell nucleic acid and protein, leaving behind a supernatant containing the plasmid nucleic acid. In an alternative, preferred embodiment, iodine may be generated in situ in the precipitating buffer through reaction of an iodide salt contained therein with an oxidizing agent such as an iodate salt.

In accordance with a further object of an aspect of the present invention is a commercial kit for the preparation of plasmid nucleic acid from a host cell, the kit comprising; mild alkaline lysis reagent for lysing host cells; an iodine providing solution for precipitating host cell nucleic acid and protein and for inactivating enzymes; and a solution for precipating the plasmid nucleic acid. The plasmid nucleic acid precipitating solution is preferably a polyethylene glycol (PEG) solution.

The kit of the present invention may also contain suitable instructions for use as well as any equipment such as centrifugation tubes and support rack as required by the method. The kit may also optionally include a cell resuspension buffer, a solution of guanidinium carbonate in a mixture of alcohol and water to allow the removal of nicked plasmid DNA from the precipitated supercoiled plasmid and a final rinse solution. The PEG solution may optionally include a reagent for the reduction of residual iodine and for controlling the pH. The mild alkaline lysis reagent may also contain an iodate salt for later oxidation of iodide to iodine.

In accordance with a further object of an aspect of the present invention is a method for the inactivation of nucleases using iodine, the method comprising: providing iodine to a suspension of plasmid nucleic acid; and incubating the iodine and plasmid nucleic acid suspension for a time sufficient to inactivate nucleases.

BRIEF DESCRIPTION OF THE DRAWINGS

A detailed description of the preferred embodiments are provided herein below with reference to the following drawings in which.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENTS

The present invention provides a simple, rapid and cost-effective method for the preparation of substantially purified plasmid nucleic acid which can be used for several applications in biotechnology.

Briefly, the method comprises mild alkaline lysis of host cells containing a plasmid, inactivating enzymes and co-precipitating proteins using a solution providing iodine and lastly, recovering the plasmid nucleic acid by polyethylene glycol (PEG) precipitation. It is understood by those skilled in the art that in the method of invention described herein precipitated materials may be separated from soluble components by any suitable technique, such as filtration, in addition to or in place of centrifugation and that exact concentrations of buffer components and volumes of reagents may vary.

More specifically, in the preferred method of the present invention host cells are collected by centrifugation, resuspended in two times a standard volume of a resuspension buffer. The cells are then lysed at room temperature (about 21 to 25° C.) by the addition of three times the standard volume 0.1M NaOH in 1–2% weight per volume (w/v) sodium dodecyl sulphate (SDS), 25 mM sodium iodate (NaIO$_3$) and 10 mM sodium ethylenediaminetetraacetate (EDTA). The amounts of EDTA and SDS used may vary but must be sufficient to promote lysis of the bacterial cells and promote precipitation of the protein components during the next step in the protocol. Sodium iodate consumes 6 moles of hydrogen ion per mole of sodium iodate during reaction with iodide according to the equation:

Although the concentration of this reagent may be varied, compensating adjustments to the concentrations of other buffer components will be necessary.

Figure 2:
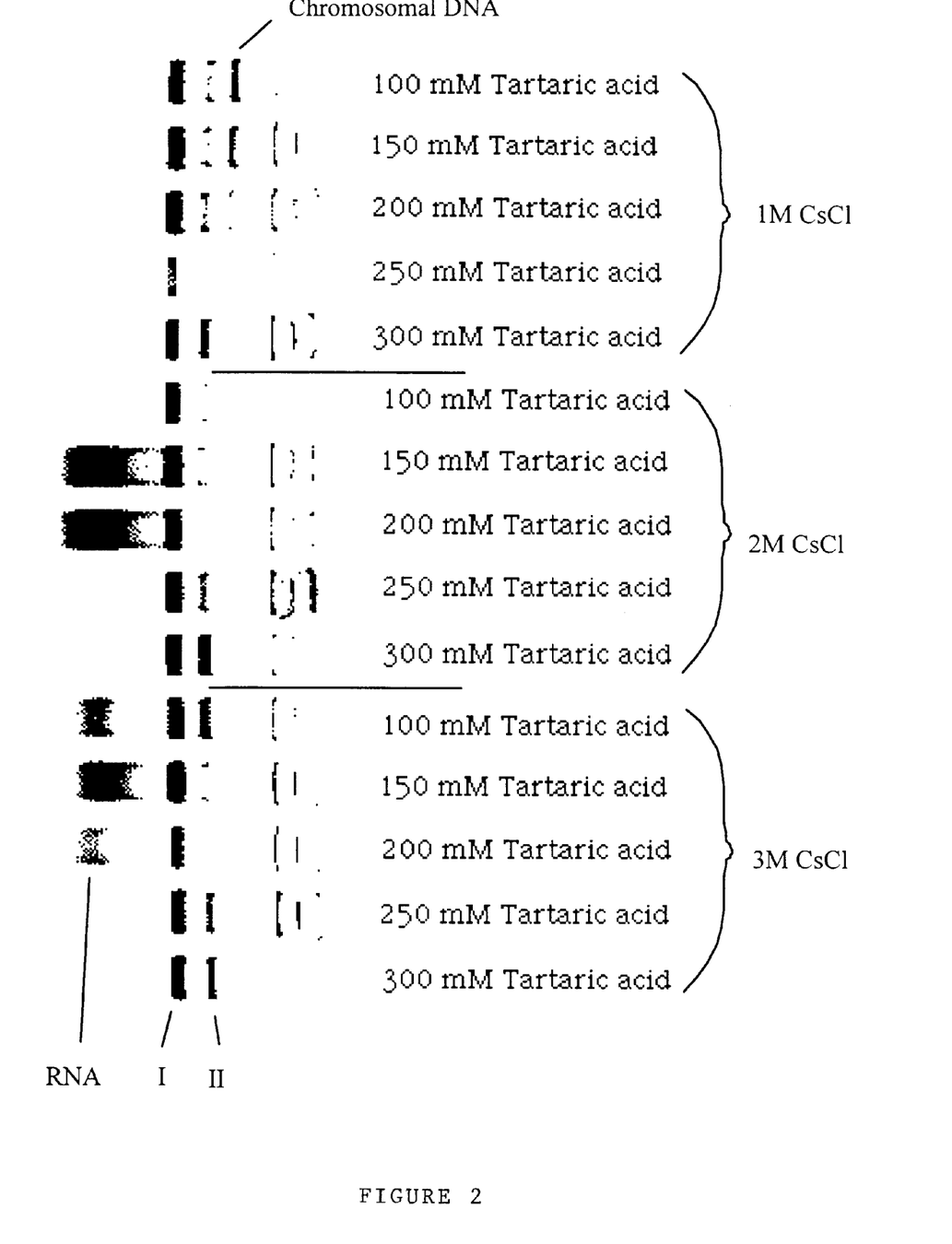
FIG. 2 shows the effects of Tartaric acid and cesium chloride concentration added in step 3 of the method on the final recovery and purity of plasmid.

Then four times the standard volume of a solution containing 2.5M CsCl, 0.25M NaI and 0.25M tartaric acid is added. The sodium iodide present in this solution reacts with the sodium iodate present in the lysis solution to produce a solubilized iodine solution. The solubilized iodine solution inactivates enzymes such as RNAase and Endo1 as well as helps to co-precipitate proteins. The concentration of sodium iodide should be in sufficient excess over the iodate salt already added so as to permit the iodine produced to form the soluble triodide complex according to the equation:

The cesium chloride is for the specific purpose of causing the precipitation of cesium dodecylsulphate and of preventing the adsorbtion of plasmid nucleic acid to that precipitate. Although the concentration of cesium chloride may be varied over a considerable range, 2.5M has been found to be near optimal (FIG. 2). The tartaric acid buffer component present in this solution assists the precipitation of cellular components other than plasmid nucleic acid by controlling the pH of the solution. The result is a precipitated DNA/RNA/protein/iodine/potassium dodecyl sulphate complex which is readily centrifuged to a pellet. It is understood by those skilled in the art that other buffer components can be used for these same purposes. The iodine is safe to use and relatively non-toxic and obviates the requirement of silica adsorption as is necessary in many commercial alkaline lysis methods.

The plasmid is recovered in the remaining supernatant and precipitated by addition of five volumes the standard volume 40% w/v PEG2000 in aqueous 3M ethanolamine solution and then centrifuged to produce a pellet. It is understood that other polymers in other buffers together with other reducing materials may be used to achieve the same purpose. This pellet of plasmid DNA is then rinsed with an alcohol water mixture to remove residual supernatant, drained, dried and then redissolved in a selected storage buffer (such as a Tris/EDTA/NaN$_3$ buffer) to permit plasmid storage at room temperature for several months and even years.

The exact concentration and volume of the PEG solution used in the method depends on the molecular weight of the PEG that is used and the total salt concentration. For example after addition of the PEG solution to the supernatant containing plasmid from the previous step the final concentration of PEG8000 should be about 7–9% w/v. PEG4000 and PEG2000 may also be used, in the method of the invention at about 10 and 14% w/v final concentration, respectively. Of these different molecular weight fractions PEG2000 is preferred as it allows a wider range of final concentrations over which the plasmid DNA may be selectively precipitated in the presence of RNA.

For users who require plasmid preparations that consist only of supercoiled DNA molecules, nicked DNA molecules may be removed by selective elution from the precipitate by a solution containing guanidinium carbonate (about 50 mM in guanidinium ion) in a mixture of approximately 60% isopropyl alcohol v/v in water. When both supercoiled and nicked plasmid DNA are desired the rinse solution may consist of a simple mixture of water and an alcohol.

It is understood by those skilled in the art that the alcohol used for rinsing of the centrifuiged pellet can be selected from isopropanol, n-propanol or ethanol at a concentration of up to about 85% v/v. It is preferred that the concentrations of alcohol used is about 70–80% v/v. Lower concentrations of alcohol in the rinse solution may result in dissolution and loss of the plasmid while higher concentrations may cause the solid precipitated plasmid DNA to detach from the surface of the centrifuge container.

The plasmid for use in the present invention may include for example but is not limited to prokaryotic and eukaryotic vectors, cloning and expression vectors and pBR322 and pUC vectors and their derivatives. The method may also be used to prepare the replicative forms of bacteriophages such as M13 or viruses such as polyoma and SV40 when such are found intracellularly in a covalently closed circular state.

The host cells used and lysed as part of the method of the invention can include for example bacterial cells, yeast, fungi, mamimalian and insect. Preferred cells are microbial cells, most preferably *E coli*. Any suitable strain of *E. coli* is contemplated.

The plasmid as used in the method of the present invention may contain a wide variety of genes encoding different types of proteins or RNA. The genes may constitute genomic DNA, cDNA, synthetic DNA, polynucleotide and oligonucleotide sequences. The sequences may be obtained via gene manipulation or via chemical synthesis as required. The plasmids may be incorporated into a suitable desired host by any known gene manipulation techniques as is well known by those skilled in the art. Similarly, the culturing of plasmid DNA-containing host is carried out using well known methods to those skilled in the art and depends on the particular host selected.

Figure 3:
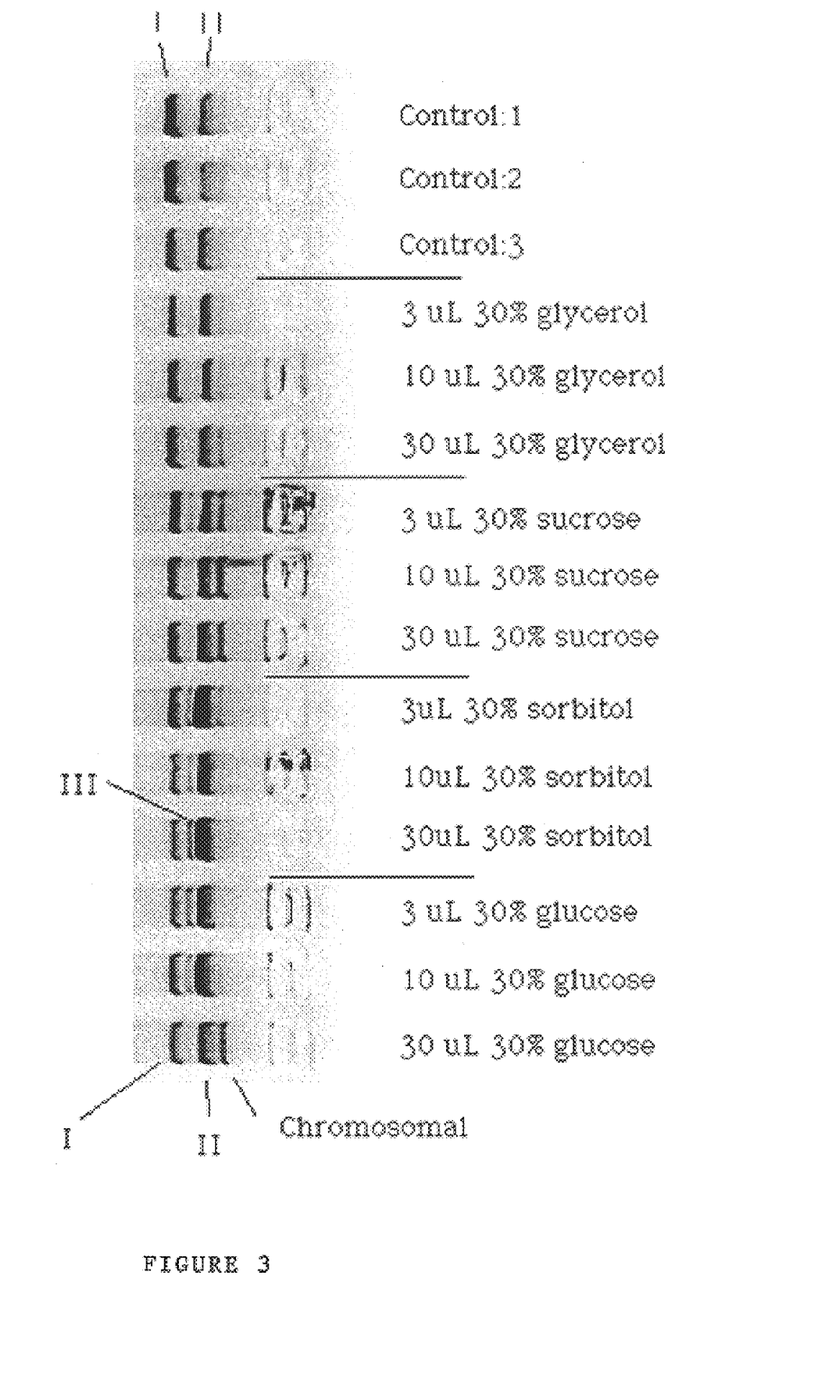
FIG. 3 shows the effects of polyhydric alcohols and sugars used to control osmolarity in the cell resuspension buffer on the formation of nicked DNA during the preparation of plasmid.
Figure 5:
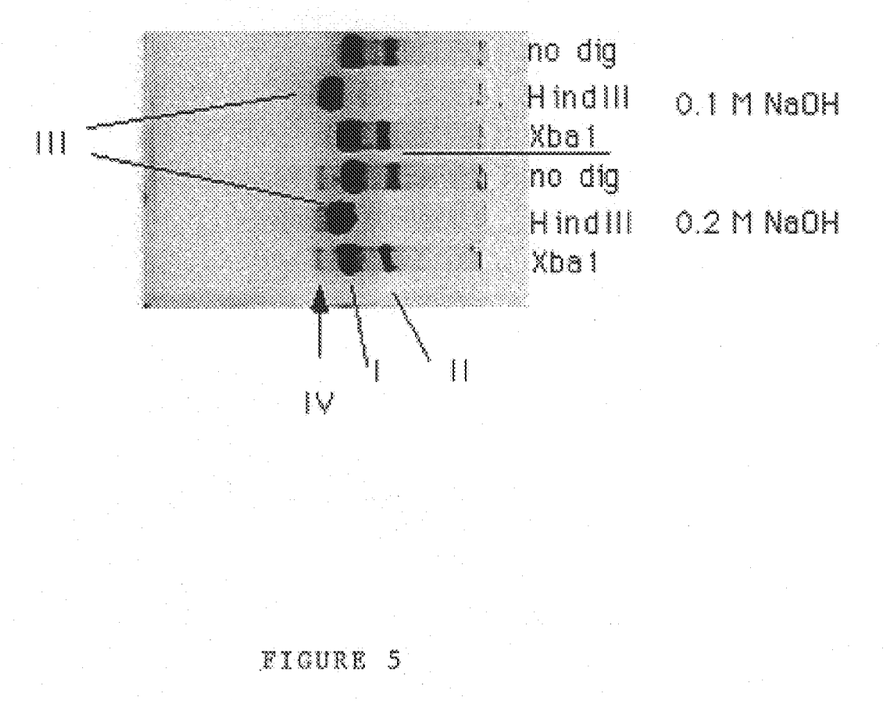
FIG. 5 shows the effect of reducing the sodium hydroxide concentration during cell lysis from 0.2 M to 0.1 M.

In the conventional alkaline lysis method of Bimboim and Doly 1% glucose was used in the cell resuspension buffer because of its buffering capacity under the extremely alkaline conditions of cell lysis. At room temperature this buffering capacity is not sufficient to prevent some denaturation of the plasmid (FIG. 5). In the method of the present invention the buffering capacity is not necessary when the sodium hydroxide concentration in the added lysis solution is reduced to 0.1M. The sodium hydroxide concentration in the lysis solution may vary from about 0.066 M to about 0.13M. The glucose present in the cell resuspension buffer of Birnboim and Doly offers an osmoprotective effect when handling cells which are sensitive to osmotic lysis in the presence of EDTA. Although glucose can be used in the resupension buffer in the present method, it is a reducing sugar which reacts slowly with iodine and with DNA under alkaline conditions therefore 1% glycerol as osmoprotectant is preferable as shown in FIG. 3.

Unlike the Bimboim and Doly technique and most other plasmid DNA preparation techniques, the novel method described herein does not require use of ribonuclease A to degrade cellular RNA. In the acidic conditions of the cesium dodecylsulphate precipitation step much of the cellular RNA is removed with the precipitate. In addition, the polyethylene glycol precipitation step as performed under alkaline conditions described in the present method, almost all remaining cellular RNA remains in the supernatant. If excessive quantities of bacterial cells are processed in relation to the stated reagent volumes, contamination of the final DNA preparation by low molecular weight RNA may occur. This is because removal of low molecular weight RNA from the plasmid by selective PEG precipitation depends on the greater solubility of this RNA in relation to plasmid DNA and it is possible to exceed the solubility limit of the RNA. Trace contaminating RNA if present, and considered to be a problem for the intended application of the DNA, can be ablated during the cell lysis stage through inclusion of 10 micrograms/mL ribonuclease A in the cell resuspension buffer. Ribonuclease A is an extremely undesirable enzyme in laboratories where RNA is used.

Figure 6:
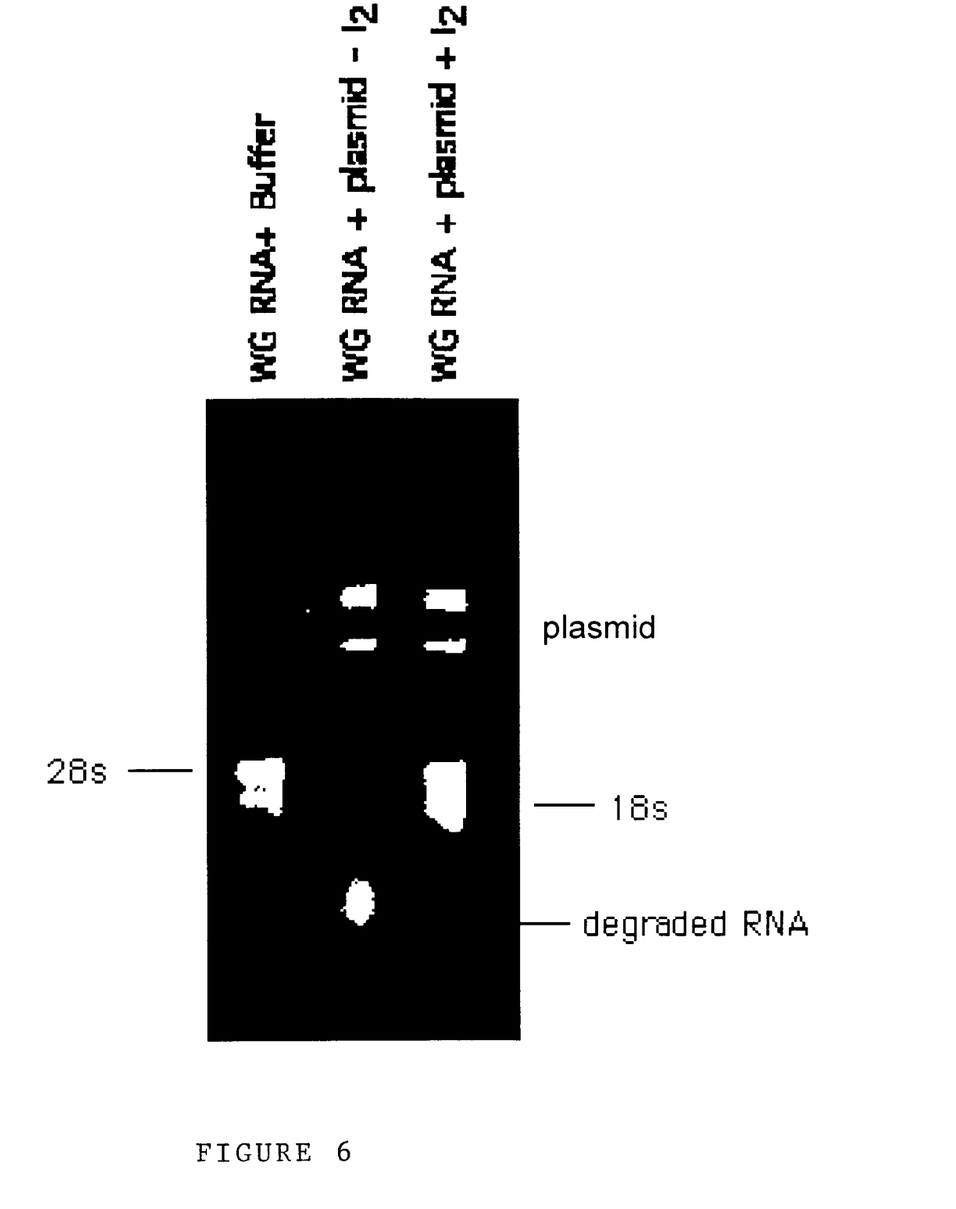
FIG. 6 shows the Inactivation of RNase by iodine.
Figure 7:
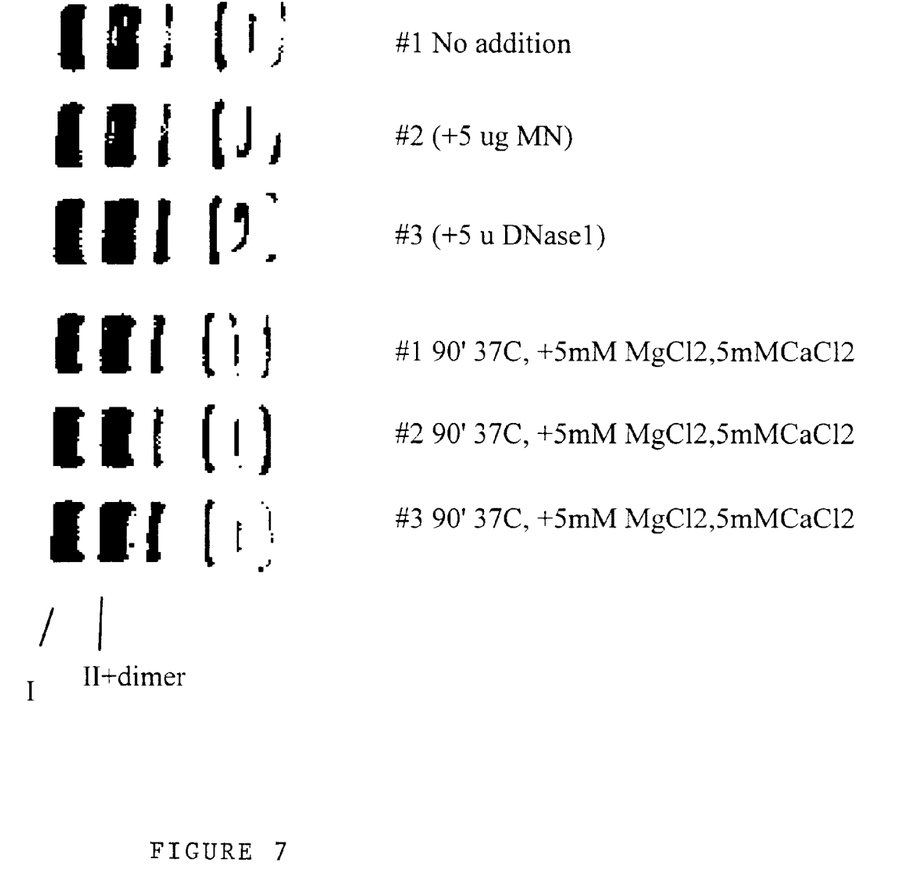
FIG. 7 shows the inactivation of Endo1 and other non-specific nucleases by Iodine.

In the preferred embodiment of the present invention, the use of Ribonuclease A is avoided and therefore the method of invention has far more use in laboratories where RNA is studied. It should be noted that even if ribonuclease is used during the preparation, the DNA will be free of ribonuclease contamination because it, along with Endo I, is irreversibly inactivated by the action of iodine (FIGS. 6 and 7).

The concentration of NaOH used in the method of the present invention is less that the 0.2M originally recommended by Bimboim and Doly and which is used in other published variations of the original protocol. This reduction in NaOH concentration permits the bacterial lysis to be performed at room temperature without the conversion of plasmid to the permanently denatured form (herein referred to as form IV). As shown in FIG. 5 a trace of form IV is present in the final preparation when cellular lysis is performed at 23° C. with 0.2M NaOH in the lysis buffer even when glucose is present (see above). Form IV can be a serious contaminant in plasmid preparations since it resists cleavage by restriction endonucleases and has a gel mobility sufficiently similar to that of the linear form of the plasmid that it may fail to separate from it during electrophoresis as shown in FIG. 5. Since denatured form IV transforms bacteria with high efficiency it is a very frequent cause of unacceptably high backgrounds during cloning experiments when plasmids prepared by an alkaline lysis technique is used (5). Detection of this nuisance is enhanced by the use of SYBR green II (Molecular Probes Inc.) in place of ethidium as a fluorophor. Because the concentration of sodium hydroxide used for cell lysis is important, the present method employs a mild (100 fold) dilution of a commercially prepared standardized sodium hydroxide solution (e.g. 10M sodium hydroxide ACP Chemicals Inc. Montreal) to prepare the lysis mixture. The working solution is stored in sealed plastic rather than glass containers because of the risk that it could become contaminated by silica or carbonate.

Figure 1:
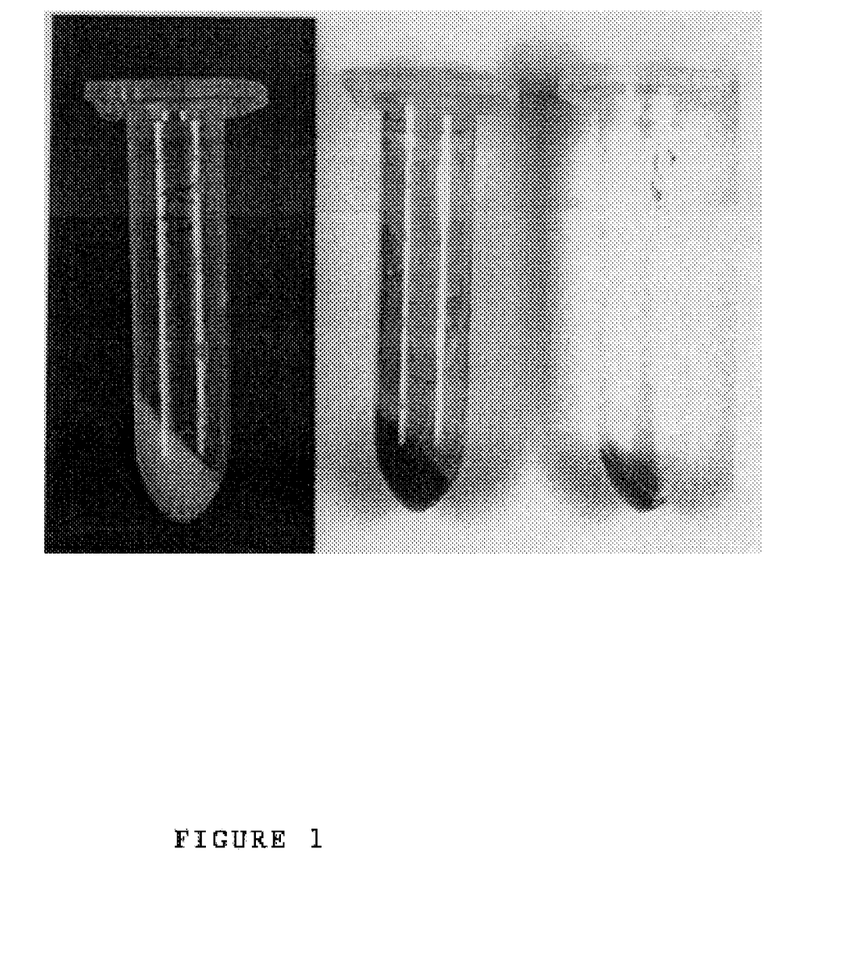
FIG. 1 shows a comparison of nucleic acid/protein/dodecyl sulphate pellets obtained in step 3 prepared from equivalent samples of bacterial cells either in when iodine was not present in an potassium acetate precipitation buffer (left) or when Iodine was added (center) or when both iodine and cesium chloride were used (right).

Iodine, introduced in the present method either as a solution of elemental iodine or generated in situ through reaction of an oxidizing material, preferably iodate, with an iodide salt, serves the dual purposes of permanently inactivating enzymes, which include Endo I (and Ribonuclease A if used) by massively iodinating tyrosine and by reacting with other amino acid residues including cysteine and tryptophan; and of enhancing precipitation of proteins along with dodecyl sulphate and denatured host cell DNA. Free iodine associates with the precipitate as evidenced by the brown colour of the precipitate and increases the density and cohesiveness of the pelleted material (FIG. 1). Removal of the supernatant which contains the plasmid by pouring is thereby facilitated. DNA is sufficiently unreactive that exposure to iodine has no effect upon it.

Versions of alkaline lysis procedures presented by some authors (1,4) use sodium acetate as the precipitating agent. It is understood that a variety of other salts as alternatives to potassium acetate or cesium chloride and detergents as alternatives to sodium dodecylsulphate may also be used in the method of the present invention as long as the detergent has low solubility in the presence of the salt. It is understood that the buffer component should be effective within a range including pH 2.5 and 5.5. In the present invention the use of a cesium salt is preferred because the high density of cesium dodecylsulphate facilitates removal of the precipitate by centrifugation and because high concentrations of cesium ions minimize interaction between plasmid DNA and the precipitated material as shown in FIG. 2 by the improved yield of plasmid obtained when more than 2M cesium chloride is present in the precipitation solution. In the present invention tartaric acid and its salts are the preferred buffer components because of non-toxicity, wide range of buffering activity, non-volatility and low reactivity with iodine.

Polyethyleneglycol (PEG) precipitation of DNA is very sensitive to the concentration and molecular weight of the PEG. Reduction of the final concentration of PEG2000 to about 11% w/v instead of 14% w/v or of PEG4000 to 7% w/v instead of the 10% w/v or of PEG8000 to 6% w/v from the 8% w/v recommended herein is sufficient to completely abolish precipitation of the DNA. 7% w/v PEG8000 precipitates the DNA but requires a longer incubation before centrifugation. PEG is not a homogeneous material. It is possible that some variation necessitating optimization may be encountered between different lots. Raising the concentration of PEG2000 substantially above 14% w/v or of PEG4000 above 10% w/v or of PEG8000 above 8% w/v does not enhance the recovery of DNA and may lead to increased contamination of the preparation by RNA.

Figure 4:
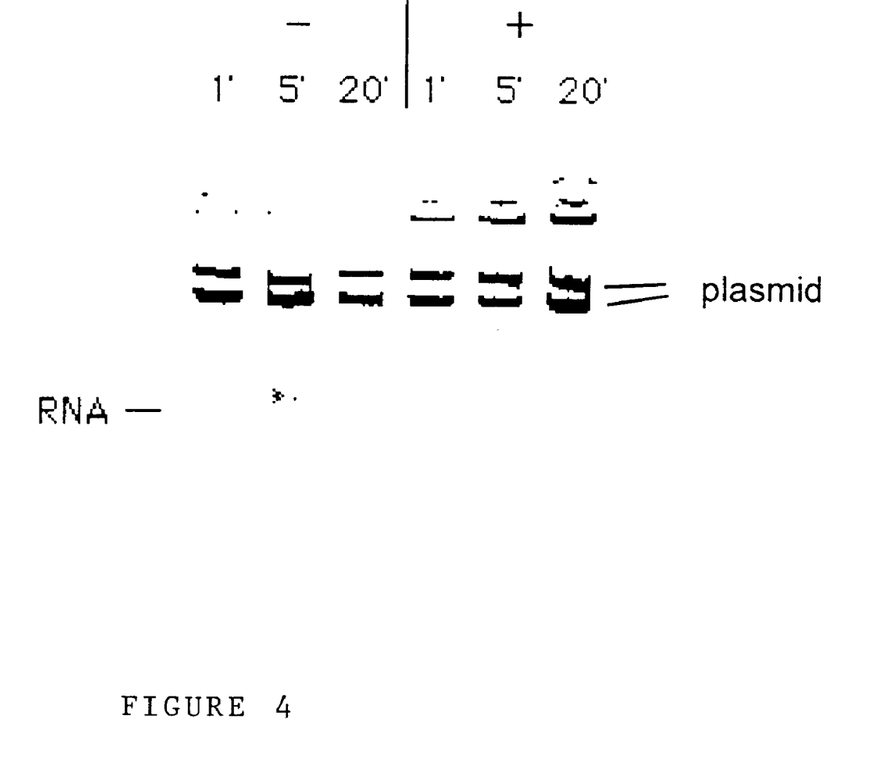
FIG. 4 shows the effect of ethanolamine and time of incubation on the selectivity of PEG6000 precipitation (10% final concentration).

The ethanolamine added along with PEG during precipitation has two functions. It reacts with the residual iodine which would otherwise form an insoluble complex with the PEG. It also raises the pH of the precipitation mixture to approximately 9.5, where, by preventing aggregation of RNA, it improves the purity of the precipitated plasmid (FIG. 4). PEG precipitation is size selective and can efficiently separate the plasmid from RNA and other lower molecular weight contaminants.

The resultant nucleic acid is substantially pure such that it can be used in a variety of biotechnology applications: gene therapy, sequencing and restriction digestion, in vitro transcription reactions, etc. The purified plasmid DNA need not be further manipulated if used for direct sequencing and restriction digestion. The final plasmid preparations may be tested for the presence of pyrogens and then suitably treated and further purified of any detected pyrogens prior to use in mammals. For example, any residual non-nucleic acid components can be adsorbed to a silica gel or a hydrophobic matrix such as charcoal. As DNA does not itself adsorb to these matrices under low ionic strength conditions, such an additional step is not the same as silica binding performed at high ionic strength as is commonly used in other plasmid purification methods (6).

In one embodiment of the present invention is a kit comprising the reagents as required along with the proper instructional material for use of such kit. It is understood that variations of the kit can be made where certain laboratory items such as suitable microfuge tubes for example, can be included therein. In another embodiment of the present invention is a system for providing substantially purified plasmid nucleic acid from host cells which comprises the reagents as required. The system may be a fully automated or manual system.

To summarize, the present invention provides a novel method and kit for the preparation of plasmid nucleic acid that is simple, fast, reliable and cost-effective. The method can be conducted at room temperature and uses a solution of iodine to inactivate enzymes and to further co-precipitate host proteins and nucleic acids from the desired plasmid nucleic acid. The method requires no chromatography but rather a simple PEG precipitation following iodine treatment to isolate the desired plasmid nucleic acid.

EXAMPLES

The example miniprep is described for the purposes of illustration only and is not intended to limit the scope of the invention.

Methods of chemistry, biochemistry and general molecular biology referred to but not explicitly described in this disclosure and examples are reported in the scientific literature and are well known to those skilled in the art.

Volumes of reagents given here are for minipreparation of plasmids (1–2 micrograms) from cells grown overnight at 37° C. in 1.4 mL of nutrient medium (Terrific Broth [TB], M9 Tryptone or Luria Broth [LB]) in an open microcentrifuge container (Eppendorf or equivalent) placed in a covered rack (e.g. "BestRack", Mandel Scientific). These volumes and concentrations have been adjusted to permit the use of a repeating pipettor dispensing multiples of a standard volume (0.1 mL). The novel sequential increase in these volumes from 2 times through 3 and 4 and then to 5 times 0.1 mL is unique to this method of plasmid preparation and is intended to serve as an aid to memory for the technician. The use of a repeating pipettor together with the simple transfer of sample by pouring from one centrifuige container to another avoids the time consuming and expensive necessity of changing pipette tips for each sample transfer. These economies permit large numbers of samples to be handled in rapid sequence. Unlike other commercial plasmid preparation systems the longest centrifugation may be performed at the leisure of the investigator. Centrifugations are at full speed (14,000 rpm) in a bench top centrifuge (Eppendorf or equivalent). Since only moderate speed centrifugations are needed, the total size of the preparation can be adjusted upwards in proportion to the size of any suitable centrifuge.

Example One

Plasmid Nucleic Acid Isolation Method

Step One: Cells are collected by centrifugation (1 min 14,000 rpm). The supernatant is discarded and then the cells resuspended in 0.2 mL 10 mM Tris chloride pH 8.3, 1 mM sodium azide+1% glycerol (or 0.6% ethyleneglycol). Resuspension may be achieved by closing the tubes and placing them in a loose fitting rack which has a lid. Touching the rack to a vortex mixer set at maximum speed for approximately 1 min is usually sufficient. Complete resuspension should be achieved before proceeding to step 2.

Step Two: A solution of 0.3 mL 0.1M NaOH, 1% SDS, 25 mM $NaIO_3$, and 10 mM EDTA by a quick pipette action is added to the resuspended cells (the jet from an Eppendorf repeating pipettor provides sufficient mixing action). The lysis mixture should not be subjected to strong shearing forces after the addition as this may lead to an increase in the amount of chromosomal DNA in the final preparation. This mixture should be allowed to stand approximately 1–3 minutes only as this incubation under strongly alkaline conditions may cause slow damage to adenine and cytosine residues in DNA.

Step Three: A solution of 0.4 mL 2.5M CsCl, 0.25M NaI and 0.25M Tartaric acid is added. The tube is closed and shaken briefly but vigorously then immediately centrifuged for approximately 1–2 minutes at about 14,000 rpm. Any extended waiting before step 4 should be avoided as the approximate pH of 3.0 conditions may cause slow depurination of DNA.

Step Four: The supernatant is poured into a marked centrifuge tube which contains 0.5 mL 40% PEG2000 w/v, 3M Ethanolamine, +30 mM HCl, 1 mM ethyleneglycoltetraacetic acid (EGTA). This precipitating solution may be prealiquoted into the centrifuge tubes. The tube is then closed, shaken vigorously and then allowed to stand about 5 minutes (longer is permissible) then centrifuged about 10 minutes at about 14,000 rpm. The HCl is added to lower the pH slightly during storage of the prepared solution to slow oxidation of ethanolamine by air. The EGTA is added to octadentally chelate and thereby render inactive any trace of redox active metal ions that may catalyse air oxidation reactions during storage).

Step Five: Perform either Step 5A or 5B:

Step 5A: For the maximum yield preparation in which the nicked DNA is recovered along with the supercoiled DNA.

The supernatant is poured off and the (invisible) pellet rinsed 3x with 80% isopropanol, 20% v/v water making sure that the residual supernatant is thoroughly mixed with the rinse solution each time and then shaken out. The tubes are allowed to drain in a downward facing position onto a paper towel or other absorbent surface and then the pellets dried with the open tubes set on their sides in an oven or bacteriological incubator set at approximately 50° C. The pellets are then resuspended by briefly vortexing the closed tube with an appropriate volume of the storage buffer of choice. 0.05 mL 10 mM Tris.HCl pH 8.3, 1 mM EDTA, 1 mM $NaN_3$ permits indefinite benchtop storage. A brief centrifugation will bring droplets to the bottom of the tube.

Figure 8:
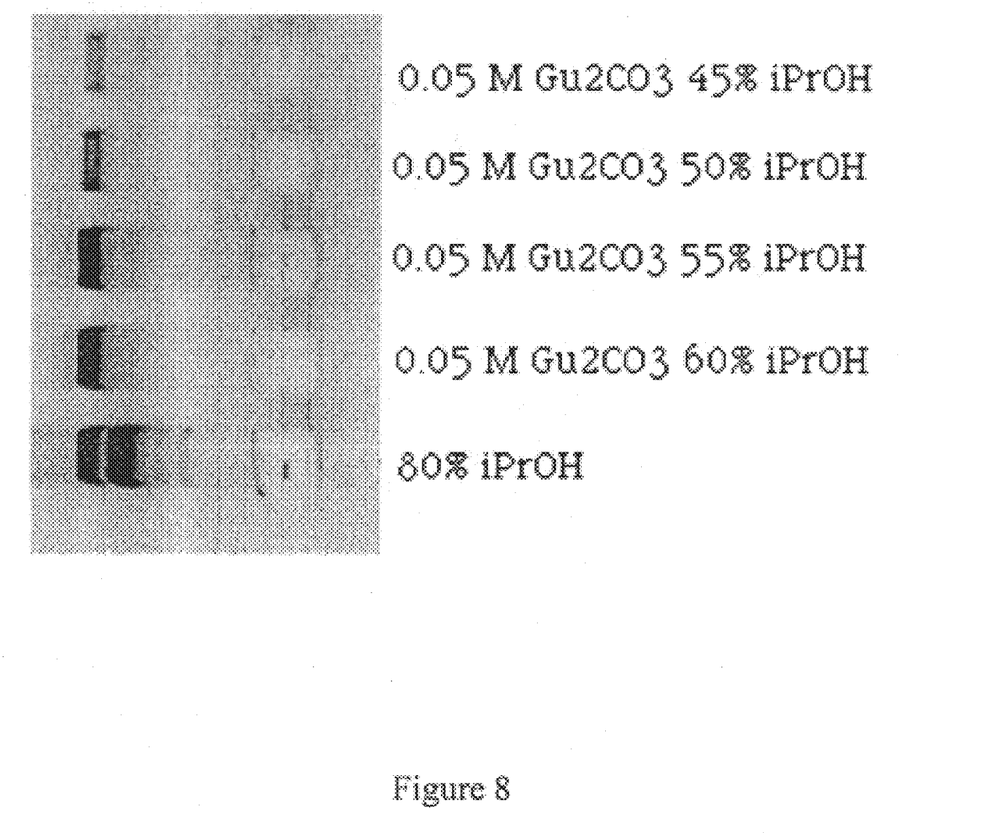
FIG. 8 shows the removal of nicked plasmid DNA from the PEG precipitate through selective solution in guanidinium carbonate (100 mM in guanidinium) in an isopropanol water mixture.

Step 5B: As illustrated in FIG. 8 for maximum purity of the supercoiled form the residual nicked plasmid may be removed by rinsing the pellet from step 4 twice with 25 mM guanidinium carbonate (50 mM guanidinium ion) in 55–60% v/v isopropanol and then once in 80% isopropanol before drying.

For minipreps the pellet is distributed over a large area of the centrifuge tube's surface and so is usually not visible.

Example Two

A comparison of nucleic acid/protein/dodecyl sulphate pellets obtained in step 3 prepared from equivalent samples of bacterial cells either in when iodine was not present in an potassium acetate precipitation buffer (left) or when Iodine was added (center) or when both iodine and cesium chloride were used (right) (FIG. 1)

The progressively more compact pellets on the center and right are the result of the insoluble material having greater density in the presence of iodine (center) or both iodine and cesium ions (right) and therefore being more effectively compressed by centrifugal force. The cells from 6 mL terrific broth culture were processed by being first resuspended in 0.4 mL resuspension buffer, lysed with 0.6 mL 0.1 M NaOH 25 mM $NaIO_3$ and then the dodecylsulphate/nucleic acid/proteins complex was precipitated with 0.8 mL of either (left): 3M KaAc/1M HAc, (center): 3MKAc/1M HAc, 50 mM $I_2$ in 100 mM KI or (right): 2.5 M CsCl, 0.25 M Tartaric acid, 0.25 M NaI. Samples were centrifuged for 1 minute at 14000 rpm. In the right hand sample all iodine was produced in-situ by oxidation of the NaI. The dark colour of the centre and right hand pellets is due to unreacted iodine which adsorbs to the insoluble complex thereby increasing its density.

Example Three

The effects of Tartaric acid and cesium chloride concentration added in step 3 of the method on the final recovery and purity of plasmid (FIG. 2)

These reagents (concentrations indicated were those present in the 0.4 mL added precipitation solution) were used for control of pH and of ionic strength during precipitation of host cell nucleic acids and protein. When (lowest group) 0.4 mL of precipitation solution containing 3 M CsCl 0.25 M NaI was added to 0.5 mL lysis mixture of 0.2 mL cell suspension+0.3 mL of lysis buffer the purest preparations were obtained when 250 mM tartaric acid was also present. More Tartaric acid (300 mM) was needed to obtain the same degree of purification when less cesium chloride (2M, center group) was used. Further reduction in the concentration of cesium chloride to 1M (top group) resulted in both lower yield of plasmid and lower purity. Under optimum conditions the pH in the final 0.9 mLs mixture was approximately 3.1. Bands I, II are supercoiled and nicked plasmid respectively.

Example Four

The effects of polyhydric alcohols and sugars used to control osmolarity in the cell resuspension buffer on the formation of nicked DNA during the preparation of plasmid (FIG. 3)

In order to emphasize the effect of conditions during alkaline lysis on the extent of nicking at the end of the preparation the lysis step was extended to 30 minutes at 23° C. After completion of the preparation according to the preferred embodiment samples were redissolved and electrophoresed in a 1% agarose gel with SYBR Green II. The triplicate control preparations without added osmotic stabilizer illustrate variability of the formation of nicked molecules (II) that results from the variable carryover of the bacteriological media into the lysis mixture. Polyhydric alcohols/sugars were added to the 0.2 mL of cell resuspension buffer (10 mM Tris.HCl pH 8.3 1 mM $NaN_3$) immediately before addition of the 0.3 mL NaOH/SDS lysis solution. Note the increased amounts of cleaved products (II=nicked, III=linear and chromosomal DNA) relative to the controls and the glycerol containing samples when lysis is performed in the presence of sucrose, sorbitol or glucose.

Example Five

The effect of ethanolamine and time of incubation on the selectivity of PEG6000 precipitation (10% final concentration)(FIG. 4)

Samples shown were prepared by 3M potassium acetate precipitation with 50 mM iodine dissolved in 0.1M potassium iodide (step 3). Plasmid DNA was recovered from the supernatant of step 3 by precipitation with PEG6000 10% final concentration. In the samples on the left residual iodine was reduced by reaction with 20 mM sodium thiosulphate during precipitation of plasmid DNA. In the right hand samples ethanolamine (0.6 M final concentration) was present during PEG precipitation. Samples were centrifuged for 10 minutes after a preliminary incubation of 1,5 or 20 minutes. Although adequate precipitation of plasmid (I,II) was obtained after only one minute of incubation for the high copy number plasmid illustrated, low copy number plasmids require longer incubation (approximately 5 minutes) for efficient recovery. Note the lack of RNA in samples precipitated in the presence of ethanolamine (+) by comparison with samples precipitated in its absence (-).

Example Six

The effect of reducing the sodium hydroxide concentration during cell lysis from 0.2 M to 0.1 M (FIG. 5)

Cells were resuspended in the glucose resuspension buffer of Bimboin and Doly. Note the presence of the denatured form IV which was not digestible by HindIII in the sample prepared in 0.2 M NaOH. Top lane in each group: no restriction endonuclease. Middle lanes of each group Hind III digenstion. Bottom lanes of each group Xba I digestion. The illustrated plasmid contains a unique Hind III site and does not contain an Xba I site. Note the lack of non-specific degradation in either sample even though the *E coli* host strain: NM522, expressed Endo I. Detection of the form IV was enhanced by the use of SYBR green II (Molecular Probes Inc.) as the fluorophor. Bands I and II , III and IV are supercoiled, nicked, linear and denatured forms of plasmid DNA respectively.

Example Seven

The inactivation of RNase by iodine (FIG. 6)

Plasmids were purified by two methods both using RNAase A at 10 micrograms/mL in the cell resuspension buffer. In the right hand sample 50 mM iodine was included during potassium acetate precipitation of unwanted cellular components. In the center lane iodine was not included in the potassium acetate buffer. These purified plasmid preparations, "plasmid+$I_2$" and "plasmid-$I_2$", respectively were incubated with wheat germ RNA in a sensitive assay designed to test for the presence residual RNAase activity. Wheat germ rRNA (0.5 micrograms in 5 microlitres of resuspension buffer: Soln A) was incubated at 37° C. for 30 min either alone or with 2 microlitres of purified plasmid dissolved in Soln A. The resulting samples were electrophoresed in the presence of SYBR green II to detect the nucleic acids. The 28s and 18s components of wheat germ rRNA were not degraded when incubated with buffer alone (left channel) or with plasmids purified by the method employing RNAase A and iodine (right channel). The rRNA was degraded when incubated with plasmids purified with RNAase and without iodine (center channel). These results show that plasmids isolated using RNAase may be contaminated by that enzyme and that iodine is effective in inactivating RNAase.

Example Eight

The inactivation of Endol and other nonspecific nucleases by Iodine (FIG. 7)

Cells from 1 mL of terrific broth culture of pUC18 in NM522 (EndoI+) were resuspended in 0.2 mL of resuspension buffer (A). #1: No exogenous nuclease, #2:5 micrograms Micrococcal nuclease (MN) (300 units Boehringer Mannheim), #3:5 Units DNaseI (Promega), were added to the respective cell samples before processing for the preparation of the plasmid. After processing by the preferred embodiment Iodine miniprep procedure an aliquot of each sample was made 5 mM each in $MgCl_2$, $CaCl_2$ and 20 mM Tris.HCl pH 8.3. After 90 minutes at 37° C. these were electrophoresed (bottom group) together with aliquots that had not been exposed to Mg/Ca (top group) in a 1% agarose gel with SYBR green II fluorescent dye for detection of nucleic acids. Note the lack of conversion of supercoiled plasmid (I) to nicked (II) during the 90 minute incubation due to either the endogenous Endo I or to residual activity of either of the added nucleases during incubation with Mg and Ca ions.

Example Nine

The removal of nicked plasmid DNA from the PEG precipitate through selective solution in guanidinium carbonate (50 mM in guanidinium) in an isopropanol water mixture (FIG. 8)

Samples were prepared with an extended alkaline lysis step to promote formation of nicked molecules during the PEG precipitation step. The plasmid precipitates were treated with various rinse solutions containing either guanidinium carbonate, water and isopropanol or with 80% isopropanol 20% water and then analyzed by agarose gel electrophoresis. Guanidinium carbonate selectively solubilizes the nicked form (II) in the presence of 55–60% isopropanol leaving the closed circular form I in the precipitate. Isopropanol concentrations of less than 55% result in loss of the supercoiled plasmid (I) from the precipitate while guanidinium carbonate is not adequately soluble in isopropanol concentrations greater than 60%. The 80% isopropanol rinse sample is included to illustrate the effectiveness with which nicked plasmid (II) is removed by the guanidinium carbonate (50 mM in guanidinium ion) rinse.

Although preferred embodiments have been described herein in detail, it is understood by those skilled in the art

References

1). Bimboim, H. C. and Doly, J. 1979, Nucleic Acids Res., 7(6),1613–23
2). Humphreys, G. O., Wilishaw, G. A., Anderson, E. S. (1975) Biochim, Biophys. Acta 1975, 383(4),457–63.
3). Pulleyblank, D. Michilak, M., Daisley, S. L., and Glick, R. (1983) Mol. Biol. Rep. 9,(3),191–5
4). Good, I., and Nazar, R. N. (1997) Biotechniques 22(3), 1123–30.
5). Sayers, J. R., Evans, D. and Thompson, J. B. (1996) Anal. Biochem. 241(2), 186–9
6). Schorr J, Moritz P, Seddon T and Schleef M. (1995) Plasmid DNA for Human Gene Therapy and DNA Vaccines. Production and Quality. Ann NY Acad Sci. Nov. 27; 772:271–3.

I claim:

1. A method for preparing plasmid nucleic acid from a host cell, the method comprising:
   lysing host cells containing said plasmid nucleic acid;
   providing iodine in sufficient quantity to inactivate host cell enzymes and ribonuclease and precipitate host cell nucleic acid and protein, leaving a supernatant containing the plasmid nucleic acid;
   precipitating the plasmid nucleic acid from the supernatant; and
   isolating the plasmid nucleic acid.

2. The method of claim 1, wherein said host cells are lysed with a solution of 0.1M sodium hydroxide in 1% SDS, 10 mM EDTA.

3. The method of claim 2, wherein said solution further comprises sodium iodate.

4. The method of claim 1, wherein said iodine is provided as a solution of iodine in the presence of an iodide salt.

5. The method of claim 1, wherein said iodine is through reaction of an iodate salt with an iodide salt in solution.

6. The method of claim 1, wherein cesium salt is used to precipitate the plasmid nucleic acid.

7. The method of claim 6, wherein tartaric acid and its salts are additionally provided to promote selective precipitation of host cell nucleic acid.

8. The method of claim 1, wherein said host cell nucleic acid and protein is precipitated at a pH of 4.0 or less.

9. The method of claim 1, wherein said method is performed at room temperature.

10. The method of claim 1, wherein said plasmid nucleic acid is precipitated from the supernatant with a solution of polyethylene glycol.

11. The method of claim 10, wherein said solution of polyethylene glycol additionally comprises ethanolamine.

12. The method of claim 1, wherein said plasmid nucleic acid is isolated by precipitation.

13. The method of claim 1, wherein said plasmid nucleic acid comprises nicked plasmid and supercoiled plasmid, said nicked plasmid being removed from supercoiled plasmid by extraction with a solution of guanidinium carbonate in alcohol.

14. The method of claim 1, wherein said isolated plasmid nucleic acid is stored in a sodium azide tris buffer at room temperature.

15. The method of claim 1, wherein said nucleic acid comprises a nucleic acid selected from the group consisting of genomic DNA, cDNA, synthetic DNA, polynucleotide sequences and oligonucleotide sequences.

16. The method of claim 1, wherein said plasmid is selected from the group consisting of prokaryotic and eukaryotic vectors, natural plasmids, cloning and expression vectors and pBR322 and pUC vectors and their derivatives and circular forms of bacteriophage and viral DNA.

17. The method of claim 1, wherein said host cells are selected from the group consisting of bacterial cells, yeast, fungi, mammalian cells and insect cells.

18. The method of claim 17, wherein said host cells are selected from a strain of *E coli*.

19. A commercial kit for the preparation of plasmid nucleic acid from a host cell, the kit comprising;
   alkaline lysis reagent for lysing host cells;
   iodine solution for precipitating host cell nucleic acid and protein and for inactivating enzymes; and
   PEG solution for precipitating the plasmid nucleic acid.

20. A method for inactivating nucleases using Iodine, said method comprising:
   providing iodine to a suspension of plasmid nucleic acid; and
   incubating said iodine and plasmid nucleic acid suspension for a time sufficient to inactivate said nucleases.

* * * * *